(12) United States Patent
Thompson

(10) Patent No.: US 7,771,363 B2
(45) Date of Patent: Aug. 10, 2010

(54) CORONARY SINUS SENSING DEVICE

(75) Inventor: Todd Thompson, San Jose, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 68 days.

(21) Appl. No.: 11/316,615

(22) Filed: Dec. 21, 2005

(65) Prior Publication Data

US 2006/0173365 A1 Aug. 3, 2006

Related U.S. Application Data

(60) Provisional application No. 60/639,148, filed on Dec. 21, 2004.

(51) Int. Cl.
*A61B 5/02* (2006.01)
(52) U.S. Cl. .................. 600/488; 600/505
(58) Field of Classification Search ........... 600/488, 600/505
See application file for complete search history.

(56) References Cited

U.S. PATENT DOCUMENTS

| 3,748,623 | A | * | 7/1973 | Millar | 338/4 |
| 4,385,636 | A | * | 5/1983 | Cosman | 600/561 |
| 4,848,926 | A | * | 7/1989 | Jenkins | 374/142 |
| 4,878,898 | A | * | 11/1989 | Griffin et al. | 604/96.01 |
| 5,046,503 | A | * | 9/1991 | Schneiderman | 600/505 |
| 6,019,728 | A | * | 2/2000 | Iwata et al. | 600/486 |
| 6,398,738 | B1 | * | 6/2002 | Millar | 600/486 |
| 6,671,560 | B2 | | 12/2003 | Westlund et al. | |
| 6,964,661 | B2 | * | 11/2005 | Rioux et al. | 606/41 |
| 2004/0049255 | A1 | * | 3/2004 | Jain et al. | 607/122 |
| 2004/0116975 | A1 | | 6/2004 | Yu et al. | |
| 2006/0074399 | A1 | * | 4/2006 | Bates | 604/522 |

FOREIGN PATENT DOCUMENTS

WO PCT/US2005/039535 10/2005

* cited by examiner

*Primary Examiner*—Patricia C Mallari
(74) *Attorney, Agent, or Firm*—Bret E. Field; Bozicevic Field & Francis LLP

(57) ABSTRACT

The present invention provides a new mechanical sensor approach to maneuvering catheters and other cardiac devices into blood outlets, with particular application to maneuvering cardiac devices into the coronary sinus and beyond. Additionally, the inventive sensing device provides assessment of the viability of branching veins and other potential device sites, such as within the coronary venous system.

6 Claims, 8 Drawing Sheets

CORONARY SINUS SENSING DEVICE

CROSS-REFERENCE TO RELATED APPLICATIONS

This application claims priority under 35 U.S.C. §119(e) to U.S. Provisional Application Ser. No. 60/639,148 filed on Dec. 21, 2004, the disclosure of which is herein incorporated by reference.

BACKGROUND OF THE INVENTION

The present invention relates generally to medical methods, apparatus and systems. More specifically, the invention relates to methods, apparatus and systems for optimizing the progression of a cardiac catheter through the coronary sinus among other venous features by monitoring blood flow.

Placement of cardiac leads in the distal branches of the coronary venous system, the great cardiac vein, or the coronary sinus provides new medical opportunities to place medical devices on the left ventricle with a much lower patient morbidity than direct placement within the ventricle. However, maneuvering devices into the coronary sinus can be a difficult task.

Deploying a pacing lead through the coronary sinus and into the distal venous system is often challenging if not impossible using standard techniques and equipment. In addition, it is often impossible to place the lead in an optimum location, for pacing or sensing cardiac electrical activity, either because there are no vessels in this region or the vasculature is too small or tortuous and therefore hard to find.

There are several reasons which make proper placement of the lead in these challenging locations difficult. These include difficulty in locating and maneuvering devices into the coronary sinus and beyond, partial obstruction of the vasculature, and unusually shaped bifurcations in the vasculature.

Prior efforts to resolve such problems included the use of stiffer guidewires, with an attended risk to the vessel walls through which the guidewire and lead are inserted. While stiffer guidewires offer additional support, they may impede advancement due to their stiffness or inability to navigate more tortuous anatomy. Leads have also been developed, such as those reported by Westlund et al (U.S. patent application Ser. No. 10/081,436 filed Feb. 20, 2002), which have sections of various stiffness, temporary locking means, and other features to expedite coronary sinus access.

Other approaches to improving coronary sinus access are an effort to detect and analyze electrical events to determine the electrodes' position, such as reported by Yu et al (U.S. patent application Ser. No. 10/729,301 file Dec. 5, 2003).

Mechanical, electrical, and fluoroscopy approaches to placement of cardiac devices into the coronary sinus and beyond have been helpful, but the need remains for a practical approach to more simply maneuver devices based on immediate, real-time local sensing. Such an advancement in the medical device arts would allow an important clinical advantage and, in some cases, availability of this important clinical approach for the first time.

REFERENCES

Patent references of interest include International Patent Application US05/39535 entitled "Cardiac Motion Characterization by Strain Measurement" filed Oct. 31, 2005, incorporated herein by reference.

SUMMARY OF THE INVENTION

The present invention provides a new mechanical sensor approach to maneuvering catheters and other cardiac devices into blood outlets, with particular application to maneuvering cardiac devices into the coronary sinus and beyond. Additionally, the inventive sensing device provides assessment of the viability of branching veins and other potential device sites, such as within the coronary venous system.

The present invention represents an entirely novel approach to detecting the optimal approach and timing for insertion of cardiac devices into the coronary sinus using a flow sensing device. While the strain sensor embodiment exemplified below presents an effective means of carrying out the present invention, other mechanical flow sensor means can also be effectively employed in the present invention, including, but not limited to, rotameter (float in tube), propeller type, thermal dilution, hot-wire anemometer and ultrasonic flow meter. Alternate flow sensor devices can also be employed in the present invention as are well recognized by the ordinary skilled artisan.

In one embodiment of the present invention, the paddle configuration of the sensor with a strain gauge provides immediate report of proximity to the coronary sinus. Additionally, the clinician has real-time feedback regarding the opening and closing of the Thebesian valve, so that the device can be inserted at the optimum moment for successful cannulation. This innovation minimizes trauma to the venous walls and valve. By reducing the time of the procedure, in some cases by several fold, the inventive device lowers potential patient morbidity and mortality secondary to the procedure.

The difficulty in locating the coronary sinus lies in the fact that the position of the coronary sinus differs from individual to individual. Increasing this challenge is that patients with advanced heart failure have an even greater variation in their heart shapes than the range within the general population. As the heart enlarges due to heart conditions, the coronary sinus tends to move down and toward the RV, resulting in the expansion of the entire structure.

The innovative sensing device dramatically increases access while minimizing trauma and placement time to this clinically valuable cardiac feature, which provides a minimally invasive access to the cardiac left ventricle. While in many cases the present invention will be a useful augmentation to existing positioning approaches, in certain instances, the sensing device will limit or eliminate the need for other placement devices and procedures.

Because of limitations to existing methods and devices, lengthy clinical efforts were typically required to gain physical access into the coronary sinus, putting patients at the attendant risk for prolonged cardiac procedures. Regrettably, such efforts often result in failure, and the valuable access to the left ventricle remains out of reach despite the effort and risk.

The simplified access to the coronary sinus system provided by the present invention will substantially increase the number of patients treated with left ventricular devices, during cardiac resynchronization therapy, resulting in improved clinical outcomes. Anticipating potential difficult access, many clinicians elect to entirely forgo the opportunities otherwise available with coronary sinus approach to the left ventricle. The underutilization of this otherwise valuable technique will now become more widely available.

DETAILED DESCRIPTION OF THE INVENTION

The inventive sensor provides methods, apparatus and systems for optimizing the progression of a cardiac catheter into a blood flow extruding cardiac feature, such as through the coronary sinus.

The difficulty with finding the coronary sinus lies in the fact that every heart is different in the spacing of anatomical features and in size and position of those features. Therefore, the position of the coronary sinus typically varies from individual to individual. The bigger challenge in cardiac feature location within a clinical setting is that people with advanced heart failure typically have a much larger variation in their heart shape than that of the general population.

In advanced heart failure, the heart enlarges, the coronary sinus tends to move down and toward the RV resulting in the expansion of the entire structure. The entire heart is enlarged and subsequently the location of the coronary sinus can be difficult to ascertain.

To date most of the work that has been done with guiding catheters for coronary sinus access has been focused on the creation of custom shaped devices that will most likely locate the coronary sinus. These custom shapes are based on the average anatomy of the heart and therefore work for many instances where the anatomy is normal. This technique also works well in instances where coronary arteries are being located, for instance when placing stents and doing angioplasty. Arteries are not blocked by valves at their openings and contrast injections can be used to find the entrance point for the catheter. The custom shapes in this environment serve two purposes: to find the artery and to keep the catheter engaged during the procedure.

In the case of the coronary sinus the blood flow is coming toward the catheter and therefore the use of contrast dye is difficult and of little use and would require the injection of a large amount of dye.

Figure 1:
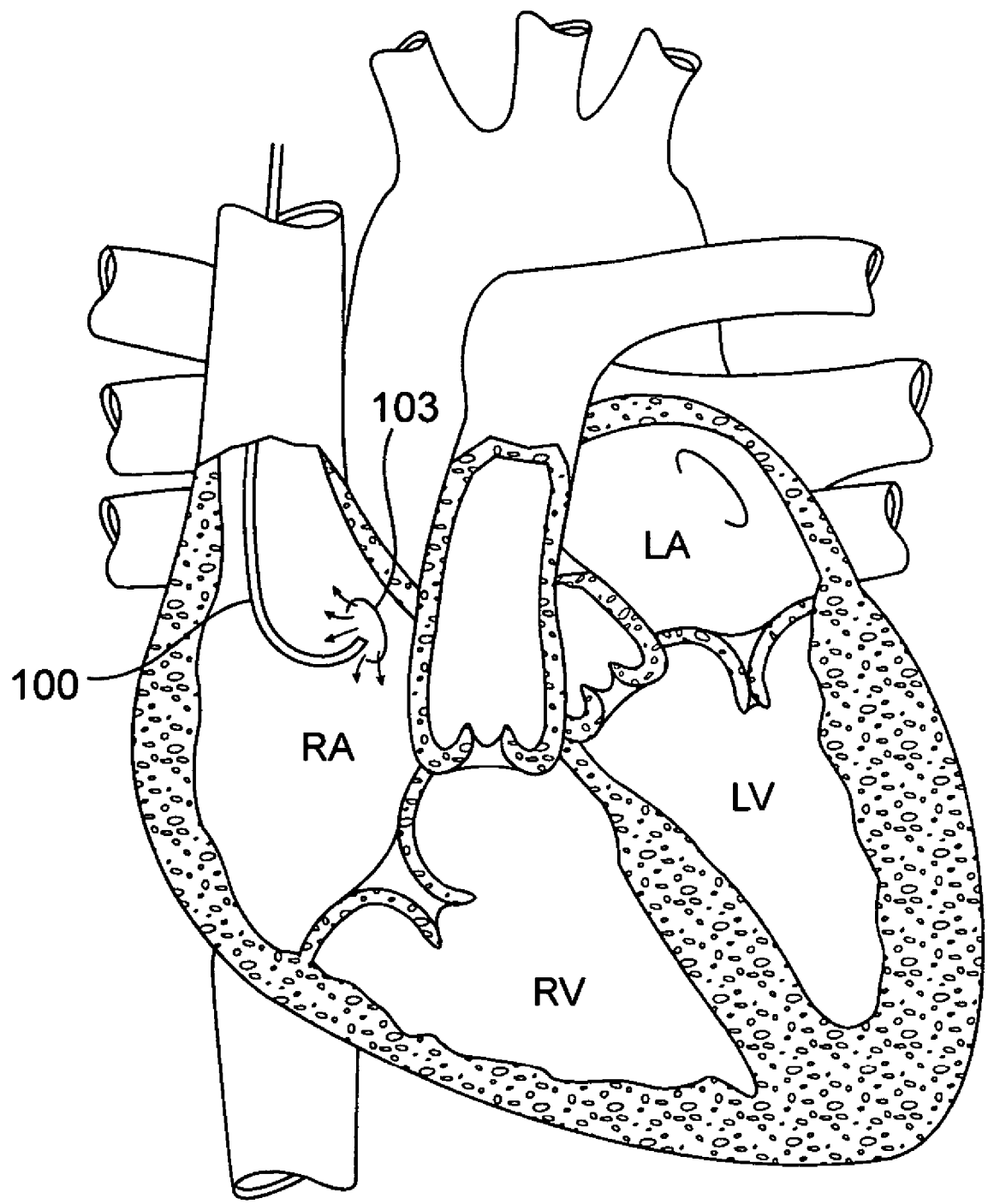
FIG. 1 provides a diagram of the coronary sinus catheter on which is the inventive coronary sinus sensor.

FIG. 1 provides a depiction of the heart showing the coronary sinus 103 with blood coming out from it, as well as a catheter 100 with the inventive coronary sinus sensor. This coronary sinus sensor device is nicknamed the coronary sinus sniffing device or the coronary sinus location device.

The coronary sinus sensor device is intended to be used in procedures where physicians are attempting to access the coronary sinus from the right atrium using a guiding catheter. This type of procedure is conducted when physicians are placing coronary sinus or venous leads for cardiac resynchronization therapy procedures. In these procedures, a third pacing lead is placed through the coronary sinus into the cardiac vein to allow pacing of the left ventricle.

The invention in this disclosure is a coronary sinus guide that uses a different approach to the anatomy. Rather than relying solely upon a special shape or combination of special shaped catheters to locate the coronary sinus, this invention utilizes the fact that blood is flowing out of the coronary sinus towards the catheter. By sensing this flow with some directionality, a catheter can be positioned in front of the coronary sinus to allow a guide or guide wire to be placed into the coronary sinus.

The invention is the use of a flow sensor, such as a sensing wing, that allows the catheter to be positioned where the flow sensing wing senses the greatest amount of flow coming from the coronary sinus.

Figure 2A:
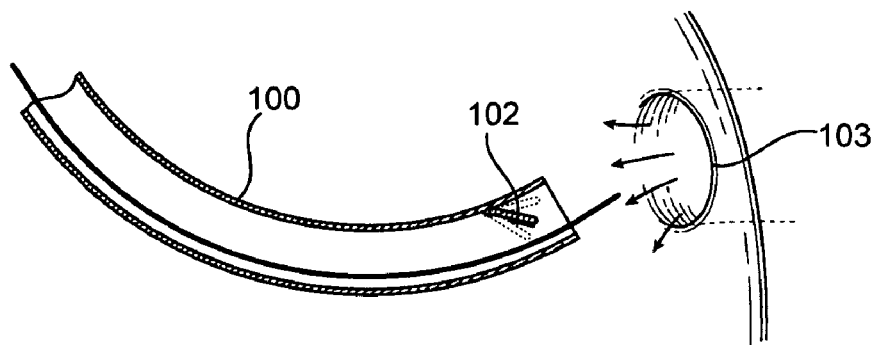
FIG. 2A-E provides diagrams of several embodiments of the inventive coronary sinus sensor.
Figure 3A:
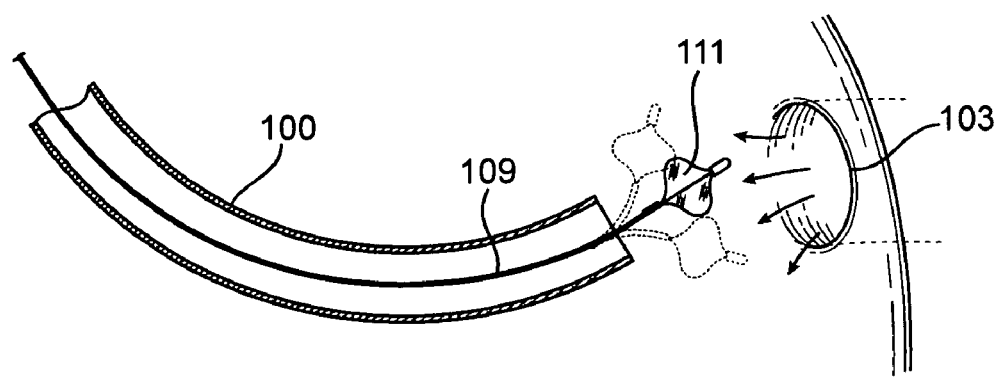
FIG. 3A-C provides a view of a deployable embodiment of the inventive coronary sinus sensor.
Figure 3B:
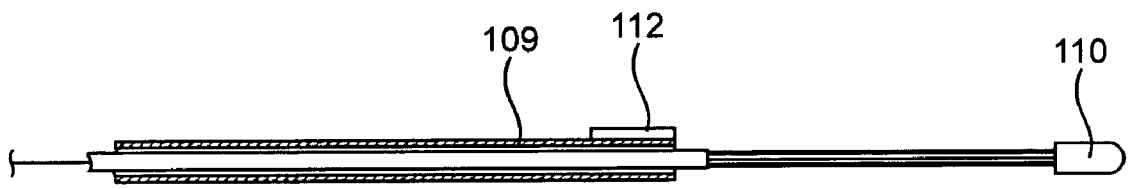

FIG. 2A shows a guiding catheter 100 with a guide wire 101 (as shown in FIG. 3B) inserted and a flow sensing wing 102 at the tip of the device. Arrows coming out of the coronary sinus 103 show the flow coming from the coronary sinus and deflecting the flow sensing wing. The flow sensing wing includes a strain sensing element as part of its design. Therefore, when the front of the catheter is aligned with the coronary sinus, the wing is deflected by the blood flow, indicating that the catheter is aligned with the coronary sinus.

Figure 2B:
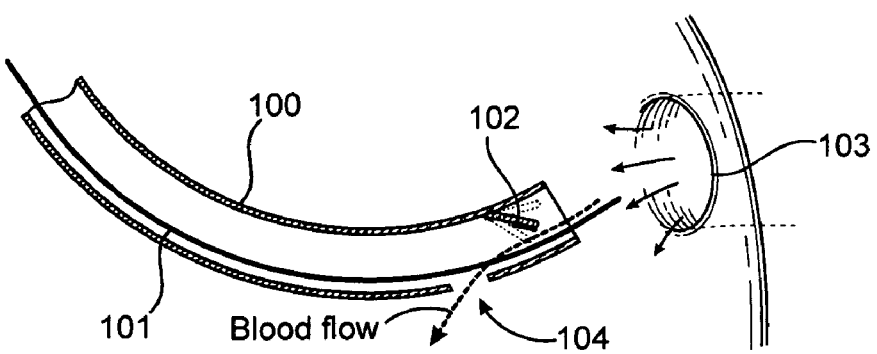

FIG. 2B provides a view of a device similar to the embodiment shown in FIG. 2a with the exception that there is an opening or a side port 104. Side port 104 allows the blood flow from the coronary sinus to enter the catheter tip and then exit behind the wing. This feature may increase the effectiveness of the wing at sensing blood flow.

Figure 2C:
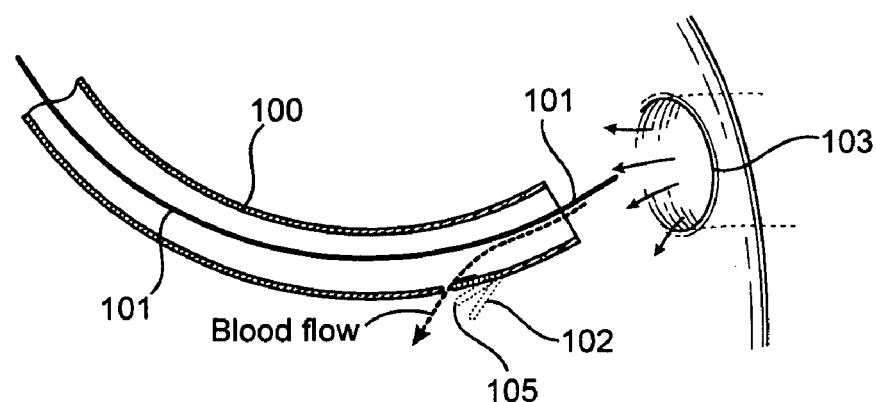

FIG. 2C shows an embodiment similar to those in 2a and in 2b. In this configuration, catheter 100 and guide wire 101 are again provided. This view further provides flow sensing wing 102 in a different orientation. In this case, the blood flow comes into the guiding catheter 100 and flows out of the guiding catheter 100 through the side port 105 and as it flows out of the side port it deflects the wing 102.

Figure 2D:
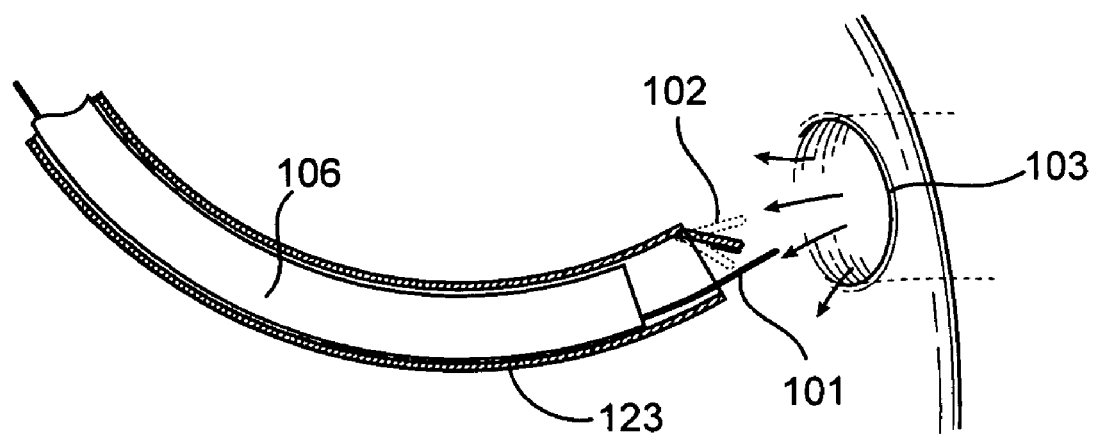

FIG. 2D shows another embodiment of the design which includes an outer guide catheter 123 and inner guide catheter 106 with a guide wire 101. The inner guide catheter 106 is deployed in front of the outer guide catheter 123 to protect the strain sensing wing 102 during insertion into the atrium. Strain sensing wing 102 is shown hanging off the tip of the outer guide catheter 100, as deployed for flow sensing. In the same way, this device allows sensing of the flow from the coronary sinus. When the catheter is aligned with the coronary sinus the flow sensing wing is deflected by the flow of blood.

Figure 2E:
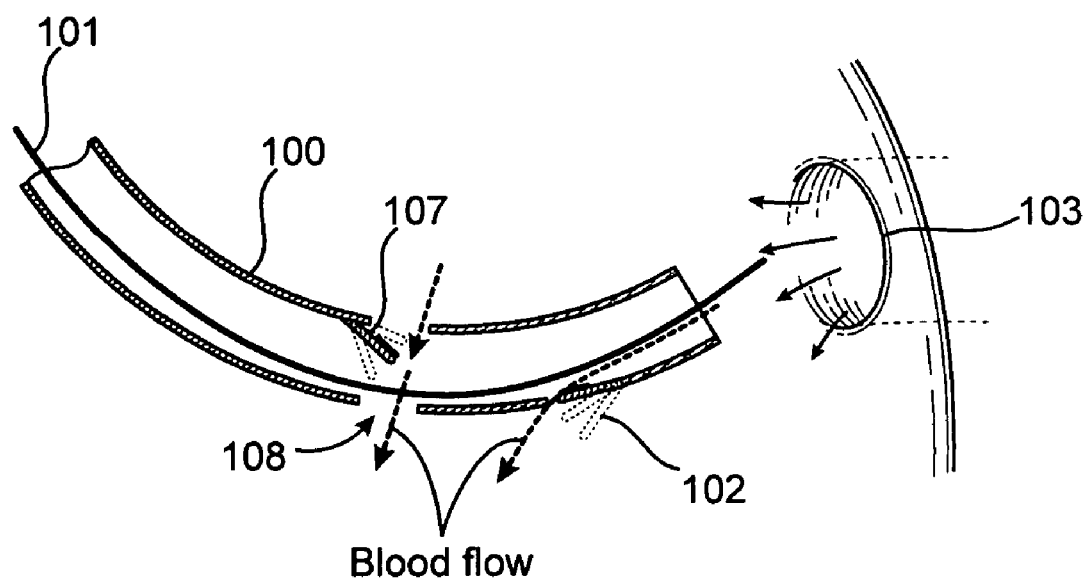

FIG. 2E shows the use a guiding catheter 100 with a guide wire 101. This particular device has two flow sensing wings deployed within it. The first one, the distal flow sensing wing 102 is closest to the coronary sinus. Distal flow sensing wing 102 is used to sense the coronary sinus flow. Proximal flow sensing wing 107 is farthest away from the coronary sinus. Proximal flow sensing wing 107 is used to sense other flow within the chamber, for instance flow from the inferior and superior vena cava. The blood flow comes into catheter 100 at the proximal wing 107 and exits the proximal side port 108. In this way any flow from the inferior and superior vena cava that is sensed by the distal flow sensor wing 102 can be subtracted out so that only the flow recorded from the coronary sinus would be sensed.

Another use of this strain or flow sensing catheter is to allow the physician to slide the guide wire forward into the coronary sinus at the appropriate time. Referring again to FIG. 2a, as the physician approaches the coronary sinus 103 the flow sensing wing will sense flow coming out of the coronary sinus 103. The flow volume amplitude will typically have a signal that is periodic in nature somewhat like a sine wave. The blood flow data will indicate when the blood flow from the coronary sinus is at a maximum and a minimum.

In many patients, there is a valve that covers the opening of the coronary sinus or a portion of the coronary sinus. This valve is termed the Thebesian valve. The Thebesian valve is like a skin flap which covers the opening to the coronary sinus. The Thebesian valve can make entering the coronary sinus very difficult when a physician is using a normal guiding catheter. He or she has no way of knowing when this valve is open or closed. Currently, clinicians rely on the catheter shape alone to get them in an area that is close to the valve. However, the clinician then has to relying on luck to slide the wire or the catheter into the coronary sinus at the appropriate time.

The present inventive system allows, for the first time, the physician to know when the blood flow is at its maximum and therefore at which point the Thebesian valve is open. If timed properly, the physician is now able to time the forward motion of the guide wire so that it enters the coronary sinus at just the time point that the flow is at the maximum, corresponding to the time point when the valve is open. This feature of the present invention will further enable physicians to access the coronary sinus more easily and more quickly in almost any clinical application regardless of the patient anatomy.

FIG. 3A shows the use of a normally shaped guiding catheter 100 with a special guide wire or a flow sensing guide wire 109 that has a retractable thin membrane wing 111. The concept embodied in this device is that the clinician slides a guide wire 109 down the guiding catheter 100. When the guide wire 109 comes out of the tip of the device, the guide wire 109 has a tip 110 (as shown in FIG. 3B). When pulled backward in the guide wire 109, tip 110 (as shown in FIG. 3B) deploys retractable wing 111.

FIG. 3B shows an enlarged view of guide wire 109 from FIG. 3A in its initial position for feeding through the catheter. In this view, the structure is shown tip 110. Strain sensing member 112 is also shown.

Figure 3C:
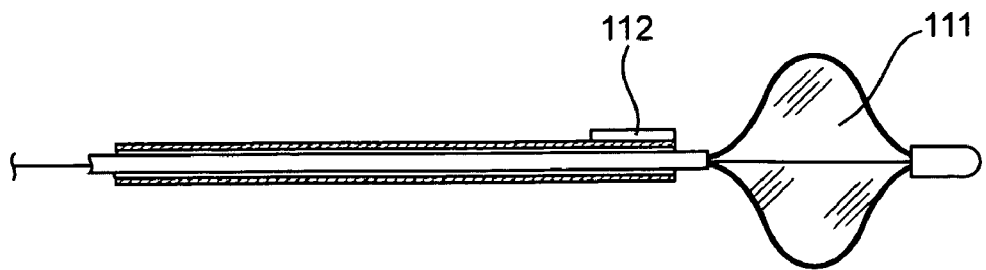

FIG. 3C shows the guide wire 109 in the position with the wing 111 deployed. In this view, the guide wire tip 110 is pulled backwards towards the rest of the guide wire 109 in the direction of the arrow. In turn, guide wire 109 deploys thin membrane wing 111. Thin membrane wing 111 is surrounded by, for instance, two pieces of wire that form the desired shape.

FIG. 3C further shows the guide wire wing 111 and its shape. The guide wire wing 111 also has a strain sensing member (strain gauge) 112 attached. In this manner, when the guide wire 109 is deflected by flow, because of the wing 111, the strain sensing member 112 senses strain. This strain data is transmitted back as an indication that the catheter 100 is aligned with the coronary sinus, as shown in FIG. 3A.

Figure 4A:
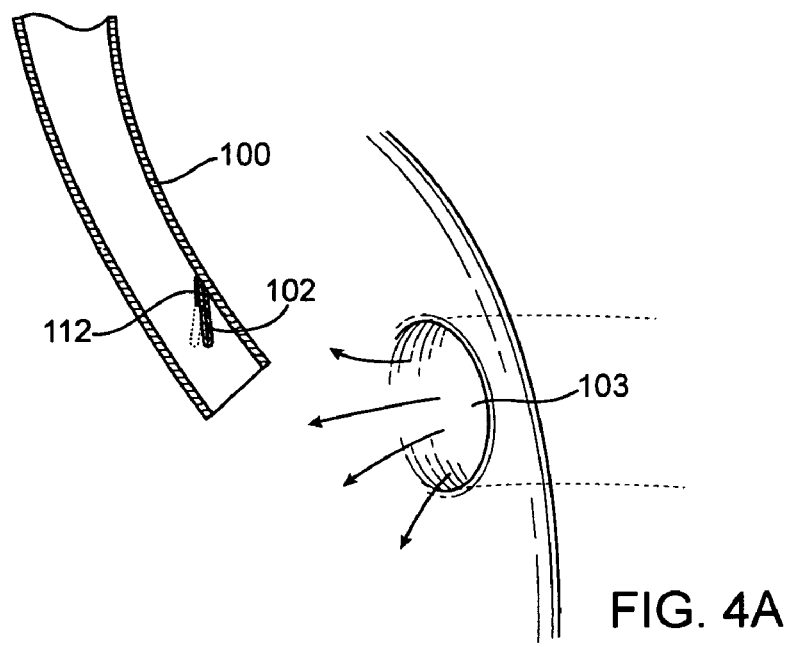
FIG. 4A-C provides a view of a rounded tip triangular winged version of the inventive coronary sinus sensor.
Figure 4B:
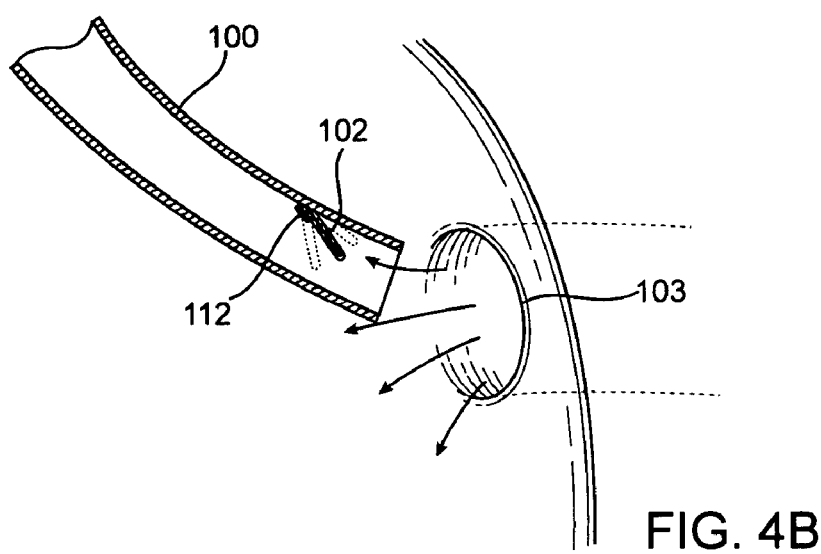

FIGS. 4A and 4B show the catheter 100 approaching the coronary sinus 103. The inventive method embodiment is conveyed in these figures. FIG. 4A shows that as the catheter 100 approaches the coronary sinus 103, the flow wing 102 senses a little bit of the flow and therefore the deflection will be minimal. In FIG. 4b, as the catheter 100 becomes more aligned with the coronary sinus 103, the flow sensing wing 102 will deflect more. This greater deflection as conveyed to the clinician from data received from strain gauges 112 is used as an indication that the catheter is well aligned with the coronary sinus 103.

Figure 4C:
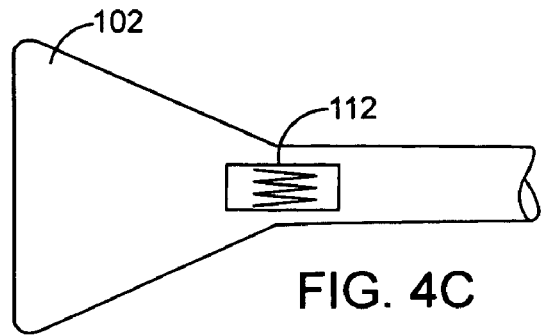

FIG. 4C shows one embodiment of a wing design with a strain gauge 112 attached to the wing 102 design. In this embodiment, a large surface area is created by providing a paddle-like wing design. The blood flow from the coronary sinus deflects the strain sensor as a result of the wing design. The thinner area of the paddle on which strain gauge 112 is positioned is most likely to bend from that coronary sinus blood flow.

Figure 5A:
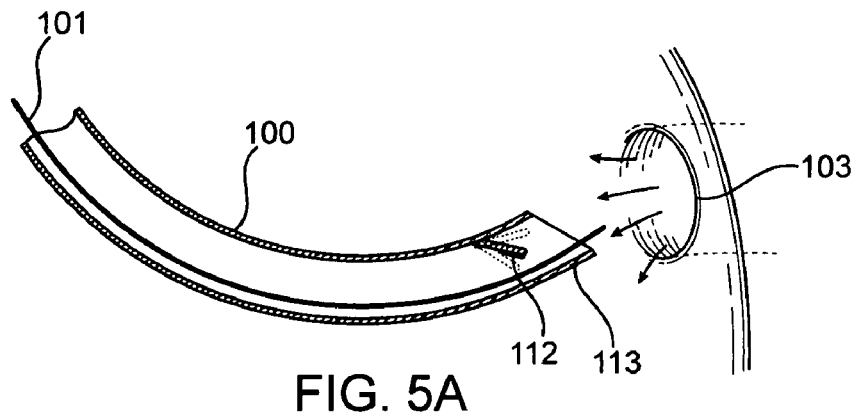
FIG. 5A-C provides a view of a diverted blood flow embodiment of the inventive coronary sinus sensor.
Figure 5B:
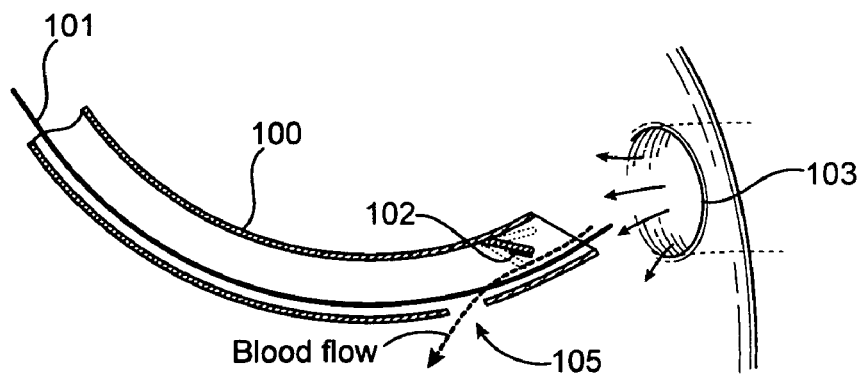
Figure 5C:
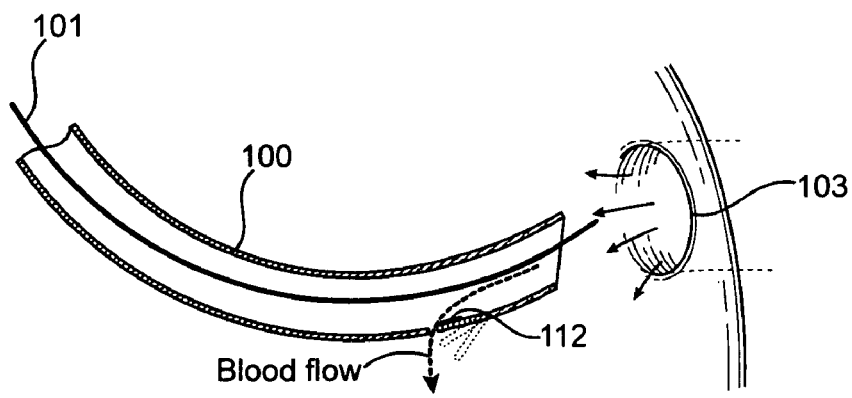

Referring to FIGS. 5A, 5B, and 5C, these figures illustrate an additional design feature of the present invention for directing blood flow to optimize blood flow sensing. The feature is a catheter that is shaped in a manner that assists in the direction of blood flow.

FIG. 5A shows an embodiment of the blood flow directing feature of the invention where the bottom lip 113 of the outer guide catheter 100 is extended so that the catheter 100 will catch and direct more of the blood flow towards the sensing wing 112. This blood directing feature can be fabricated by providing an angled cut on the tubing. Alternately, a tongue may be placed in the tip of the catheter which would scoop or direct blood into the guide catheter and direct it towards the flow sensing wing 112. Other device features to accomplish blood flow direction will be apparent to the skilled artisan.

FIG. 5B shows an embodiment similar to that shown in FIG. 5A it with the side port 105 to allow blood to come in and go out of the catheter once it passes the flow sensing wing. FIG. 5C shows again the flow being directed into the catheter 100 and towards the flow sensing wing 112. The blood flow will then come out of the catheter 100 just beyond the wing 112 arrows showing blood flow have been added for clarity.

The above described embodiments of the present invention, as well as those apparent to the skilled artisan, can be employed with a number of different types of strain sensing devices. With the present invention, how the strain is measured, or how the flow is measured is not critical. Rather, it is enough that measured flow is used to detect and locate the coronary sinus. Typical strain gauges could be used, such as a piezoelectric device, fiber optics, semi conductor strain gauges, and the like. An example providing such strain gauges is found in the provisional patent applications "Cardiac Motion Characterization by Strain Measurement" filed Dec. 17, 2004 by some of the present inventors, 60/638,247, hereby incorporated by reference in its entirety.

It is also important to note that with this particular device it may be valuable to include a pressure sensor at the tip of the device as well as the strain sensing device. The two devices in combination can be used to help begin the of the coronary sinus location process by measuring the local pressure within the right atrium. This pressure signal could also be used as a timing mechanism to time the introduction of a wire into the coronary sinus once it has been located by the coronary sinus location device of this invention.

Example 1

A prototype device similar to those show in FIG. 2A was constructed. In a water bath, a laminar flow of water was introduced from a tube to simulate flow from the coronary sinus. A periodic, moderate pulse in that liquid flow was provided. The prototype device was that directed in varying degrees towards this flow, simulating a catheter approaching the coronary sinus.

Figure 6A:
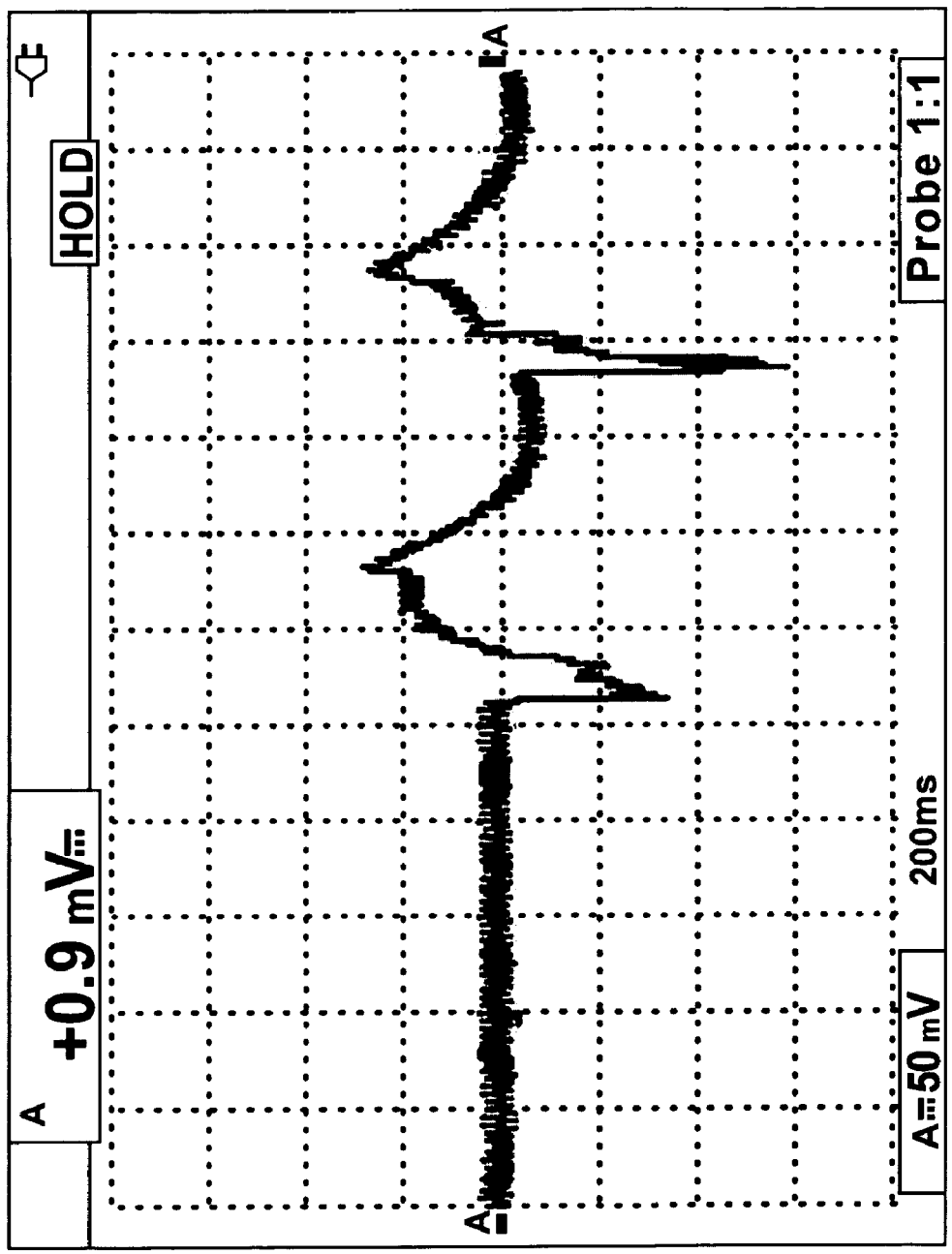
FIG. 6A-B are charts showing data from the inventive coronary sinus sensor.
Figure 6B:
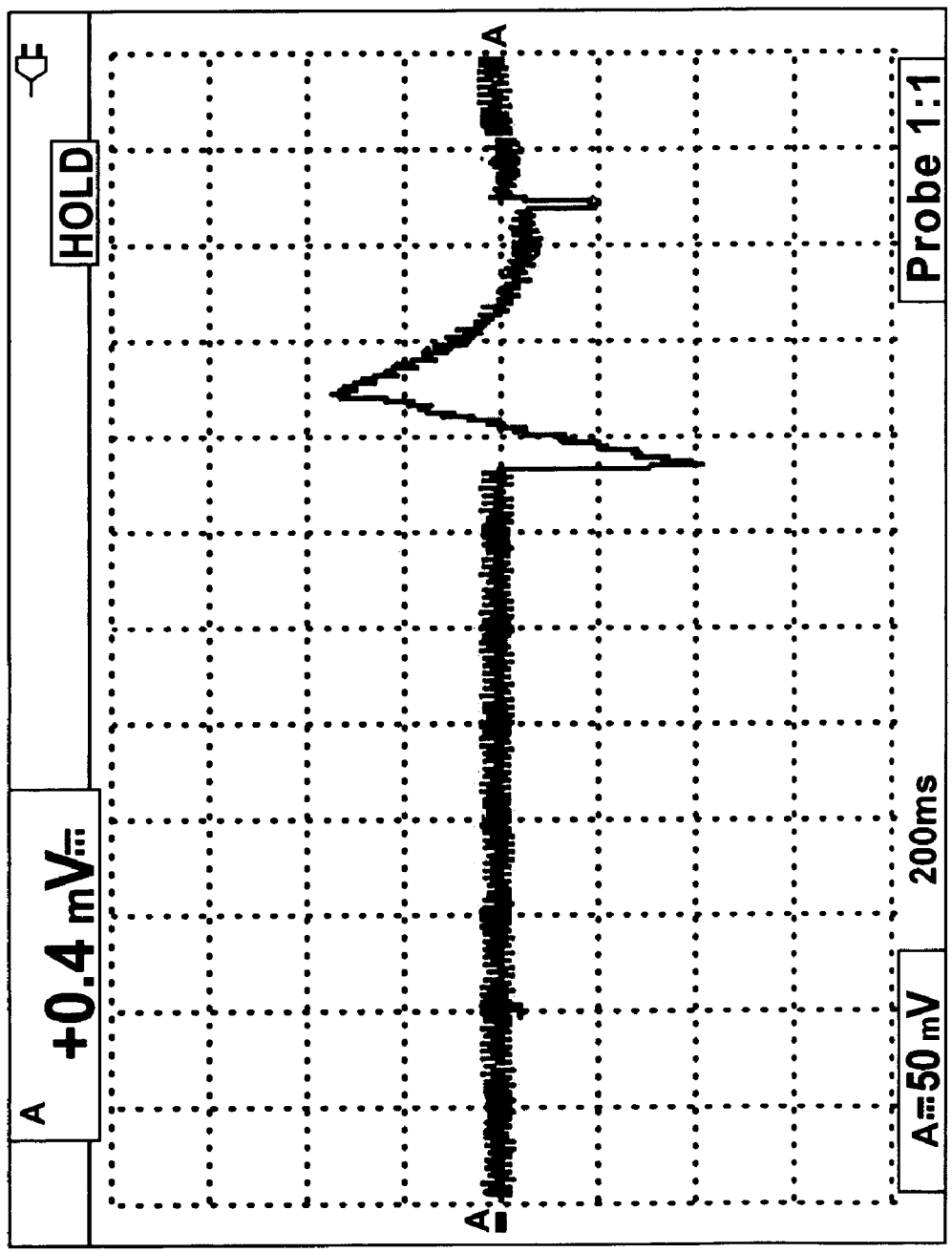

When the sensor was directed towards, but somewhat obliquely towards the coronary sinus flow, the pressure sensor provide a moderate pressure sensor reaction, such as shown in FIG. 4A. As the simulated catheter more closely approached the fluid flow, the pressure sensor reaction was considerably increased, such as seen in FIG. 4B. The data obtained during this prototype experiment is provided in FIGS. 6A&B.

What is claimed is:

1. A fluid flow outlet location device, the device comprising:
   a catheter having a proximal end and a distal end;
   a sensing wing comprising a strain gauge located at the distal end of the catheter, wherein the sensing wing extends from the catheter, is positioned in a lumen of the catheter and is directly attached at only one end to the catheter, wherein the sensing wing is configured such that the sensing wing is deflected by fluid flow when the distal end of the catheter is near a fluid flow outlet location;
   an inner guide catheter in the catheter; and
   a guidewire in the inner guide catheter.

2. The fluid flow outlet location device according to claim 1, wherein the distal end of the catheter is configured to direct fluid flow towards the sensing wing.

3. The fluid flow outlet location device according to claim 1, wherein the sensing wing has a paddle configuration.

4. The fluid flow outlet location device according to claim 1, wherein the sensing wing is configured to be in direct contact with the flowing fluid.

5. The fluid flow outlet location device according to claim 1, wherein the guidewire is positioned relative to the catheter such that the guidewire can be placed into the fluid flow outlet location when the catheter is aligned with the fluid flow outlet location.

6. The fluid flow outlet location device according to claim 1, wherein the sensing wing is configured so that deflection of the sensing wing varies in relation to the proximity of the distal end of the catheter to a fluid flow outlet location.

* * * * *